United States Patent [19]

Sirrenberg et al.

[11] 4,000,268
[45] Dec. 28, 1976

[54] N,N-DIMETHYL-N'-[O-PHENYL-(THIONO)-ALKANE-PHOSPHONYL]-FORMAMIDINES

[75] Inventors: Wilhelm Sirrenberg, Sprockhovel; Ingeborg Hammann, Colonge; Bernhard Homeyer, Opladen, all of Germany

[73] Assignee: Bayer Aktiengesellschaft, Leverkusen, Germany

[22] Filed: Apr. 22, 1975

[21] Appl. No.: 570,938

[30] Foreign Application Priority Data

Apr. 25, 1974 Germany .......................... 2420069

[52] U.S. Cl. .................................. 424/211; 260/945
[51] Int. Cl.² ...................... A01N 9/36; C07F 9/24
[58] Field of Search .................... 260/945; 424/211

[56] References Cited
UNITED STATES PATENTS 3,888,951  6/1975  Hoffmann et al. ................. 260/945

FOREIGN PATENTS OR APPLICATIONS 2,312,738  9/1973  Germany .......................... 260/945

Primary Examiner—Anton H. Sutto
Attorney, Agent, or Firm—Burgess, Dinklage & Sprung

[57] ABSTRACT

N,N-Dimethyl-N'-[O-phenyl-(thiono)-alkane-phosphonyl]-formamidines of the formula

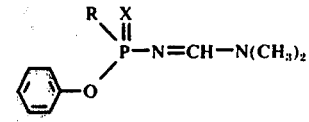

in which
R is alkyl with 1 to 4 carbon atoms, and
X is oxygen or sulfur, which possess insecticidal, acaricidal, nematocidal and fungicidal properties.

7 Claims, No Drawings

N,N-DIMETHYL-N'-[O-PHENYL-(THIONO)-ALKANE-PHOSPHONYL]-FORMAMIDINES

The present invention relates to and has for its objects the provision of particular new N,N-dimethyl-N'-[O-phenyl-(thiono)-alkane-phosphonyl]-formamidines which possess insecticidal, acaricidal, nematocidal and fungicidal properties, active compositions in the form of mixtures of such compounds with solid and liquid dispersible carrier vehicles, and methods for producing such compounds and for using such compounds in a new way especially for combating pests, e.g. insects, acarids, nematodes and fungi, with other and further objects becoming apparent from a study of the within specification and accompanying examples.

It is known from German Published Specification DOS 2,312,738 that N,N-dimethyl-N'-[O-aryl-thiono-ethanephosphonyl]-formamidines, for example N,N-dimethyl-N'-[O-4-methylphenyl-(Compound A) or -O-3-chlorophenyl(Compound B) or -O-2,4,5-trichlorophenyl-thiono-ethanephosphonyl]-formamidine (Compound C), have insecticidal, acaricidal or nematocidal properties.

The present invention provides N,N-dimethyl-N'-[O-phenyl(thiono)-alkane-phosphonyl]-formamidines of the general formula $$\text{(I)}$$

in which
 R is alkyl with 1 to 4 carbon atoms, and
 X is oxygen or sulfur.
Preferably, R is alkyl with 1 to 3 carbon atoms.

Surprisingly, the N,N-dimethyl-N'-[O-phenyl(thiono)-alkanephosphonyl]-formamidines according to the invention show a better insecticidal, including soil-insecticidal, acaricidal and nematocidal action than the previously known compounds of analogous structure and of the same type of action. Accordingly, the compounds according to the invention represent a genuine enrichment of the art.

The invention also provides a process for the production of a N,N-dimethyl-N'-[O-phenyl(thiono)-alkane-phosphonyl]-formamidine of the formula (I) in which an O-pheny(thiono)-alkane-phosphonic acid ester amide of the general formula $$\text{(II)}$$

in which
 R and X have the abovementioned meanings
is reacted with a N,N-dimethyl-acetal of the general formula $$(CH_3)_2N-CH\begin{matrix}O-Alkyl\\O-Alkyl\end{matrix} \quad (III)$$

in which
Alkyl is alkyl with 1 to 6 carbon atoms.

The reaction may be carried out in the presence of a solvent or diluent.

If, for example, O-phenylthionoethanephosphonic acid ester amide and dimethylformamide-dimethylacetal are used as starting materials, the course of the reaction can be represented by the following formula scheme:

$$\text{(IIa)} \quad + (CH_3O)_2CH-N(CH_3)_2 \quad \text{(IIIa)}$$

$$\xrightarrow{-2 \times CH_3OH} \quad (2)$$

The O-phenyl(thiono)-alkanephosphonic acid ester amides of formula (II) used as starting materials are known from the literature and can be prepared according to customary processes as described in German DOS 2,019,597. The N,N-dimethyl-acetals of formula (III) are also obtainable as described in the literature, e.g. Berichte, Vol. 101 (1968) 46 and Zeitschrift fur Chemie, Vol. 9 (1969) 201.

The following may be mentioned as examples thereof:
O-phenyl-methane-, -ethane- and -propane-phosphonic acid ester amide and the thiono-analogs; and N,N-dimethylformamide-dimethyl-and -diethyl acetals.

The process of preparation is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride or chlorobenzene; ethers, for example diethyl ether, dibutyl ether and dioxane; ketones, for example acetone, methyl ether ketone, methyl isopropyl ketone and methyl isobutyl ketone; and nitriles, such as acetonitrile and propionitrile. The alcohol corresponding to the acetal can also be used as the solvent or diluent.

The reaction temperature can be varied within a fairly wide range. In general, the reaction is carried out at between 10° and 150° C, preferably at from 50° to 80° C.

The process is generally carried out under atmospheric pressure.

In carrying out the process, the acetal is generally employed in 20 to 30% excess and the reactants, in most cases without any solvent, are heated for one to several hours at the stated temperatures. Working up may then be carried out in the usual manner.

The new compounds are frequently obtained in the form of oils which in some cases cannot be distilled without decomposition but can be freed from the last volatile constituents by so-called "slight distillation", that is to say by prolonged heating under reduced pressure to moderately elevated temperatures, and can be purified in this way. They are characterized by the refractive index. Some of the compounds are obtained in a crystalline form of sharp melting point.

As has already been mentioned, the N,N-dimethyl-N'-[O-phenyl(thiono)-alkanephosphonyl]-formamidines according to the invention are distinguished by an excellent insecticidal, soil-insecticidal, acaricidal and nematocidal activity. They are active against plant pests, hygiene pests and pests of stored products. They have a low phytotoxicity and a good action against sucking and biting insects and mites; furthermore, some of the compounds also have a fungicidal action.

For this reason, the compounds according to the invention can be employed successfully as pesticides in plant protection and in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the current gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the bitting insects, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

The active compounds according to the invention have a low toxicity to warm-blooded animals and powerful nematocidal properties and can therefore be used to combat nematodes, especially phytopathogenic nematodes. These essentially include leaf eelworms (Arphelenchoides), such as the chrysanthemum eelworm (A. *ritzemabosi*), the leaf-blotch eelworm (A. *fragariae*), and the rice eelworm (A. *oryzae*); stem nematodes (Ditylenchus), such as the stem eelworm (D. *Dipsaci*); root-knot nematodes (Meloidogyne), such as M. *arenaria* and M. *incognita*; cyst-forming nematodes (Heterodera), such as the potato cyst eelworm (H. *rostochiensis*), and the beet cyst eelworm (H. *schachtii*), and also freeliving root nematodes, for example of the genera Pratylenchus, Paratylenchus, Rotylenchus, Xiphinema and Radopholus.

When applied against hygiene pests and pests of stored products, particularly flies and mosquitoes, the compounds of the invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematocides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplates those in which the active compound is present in an amount substantially between about 0.0001–10%, preferably 0.01–1%, by weight of the mixture. Thus, contemplate present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids, nematodes and fungi, and more particularly methods of combating insects, acarids and nematodes, which comprises applying to at least one of correspondingly (a) such insects, (b) such acarids, (c) such nematodes, (d) such fungi, and (e) the corresponding habitat thereof, i.e. the locus to be protected, e.g. to a growing crop, to an area where a crop is to be grown or to a domestic animal, a correspondingly combative or toxic amount, i.e. an insecticidally, acaricidally, nematocidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cc of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined as a percentage: 100% means that all the flies were killed; 0% means that none of the flies were killed.

The active compounds, their concentrations, the evaluation times and results can be seen from Table 1.

amount of emulsifier and the concentrate was diluted with water to the desired concentration.

Bean plants (*Vicia faba*) which were heavily infested with the bean aphid (*Doralis fabae*) were watered with the preparation of active compound so that the preparation of active compound penetrated into the soil without wetting the leaves of the bean plants. The active compound was taken up by the bean plants from the soil and thus passed to the infested leaves.

Table 1

| (*Drosophila* test) | | |
|---|---|---|
| Active compound | Active compound concentration in % by weight | Degree of destruction in % after 1 day |
| $C_2H_5$ \ S \\ \|\| \\ P—N=CH—N(CH$_3$)$_2$ \\ CH$_3$—⟨⟩—O / <br>(known) (A) | 0.1<br>0.01<br>0.001 | 100<br>40<br>0 |
| CH$_3$—P(S)(O—⟨⟩)(N=CH—N(CH$_3$)$_2$)  (1) | 0.1<br>0.01<br>0.001 | 100<br>100<br>40 |
| $C_2H_5$ \ S \\ \|\| \\ P—N=CH—N(CH$_3$)$_2$  (2) \\ ⟨⟩—O / | 0.1<br>0.01<br>0.001 | 100<br>100<br>45 |

EXAMPLE 2

Doralis test (systemic action)

Solvent: 3 parts by weight of acetone
Emulsifier: 1 part of weight of alkylaryl polyglycol ether To produce a suitable preparation of active compound, 1 part by weight of active compound was mixed with the stated amount of solvent and the stated After the stated times, the destruction in % was determined, 100% means that all aphids had been killed; 0% means that no aphids had been killed.

The active compounds, active compound concentrations, times of evaluation and results can be seen from Table 2.

Table 2

| (*Doralis* test/systemic) | | |
|---|---|---|
| Active compound | Active compound concentration in % by weight | Degree of destruction in % after 4 days |
| CH$_3$—⟨⟩—O—P(S)($C_2H_5$)—N=CH—N(CH$_3$)$_2$ <br>(known) (A) | 0.1<br>0.01<br>0.001 | 100<br>100<br>10 |
| Cl—⟨⟩—O—P(S)($C_2H_5$)—N=CH—N(CH$_3$)$_2$ <br>(known) (B) | 0.1<br>0.01<br>0.001 | 100<br>98<br>0 |
| CH$_3$—P(S)(O—⟨⟩)(N=CH—N(CH$_3$)$_2$)  (1) | 0.1<br>0.01<br>0.001 | 100<br>100<br>100 |
| CH$_3$—P(O)(O—⟨⟩)(N=CH—N(CH$_3$)$_2$)  (3) | 0.1<br>0.01<br>0.001 | 100<br>100<br>100 |

EXAMPLE 3

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the destruction in % was determined. 100% means that all the spider mites were killed whereas 0% means that none of the spider mites were killed.

The active compounds, the concentrations of the active compounds, the evaluation times and the results can be seen from Table 3.

Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (=mg/l), was decisive. The soil was filled into pots and the pots were left to stand at room temperature.

After 24 hours, the test insects were introduced into the treated soil and after a further 2 to 7 days the degree of effectiveness of the active compound was determined in % by counting the dead and live test insects. The degree of effectiveness was 100% if all test insects Table 3

| Active compound | Active compound concentration in % by weight | Degree of destruction in % after 8 days |
|---|---|---|
| $C_2H_5$, $CH_3$—⌬—O, P(=S)—N=CH—N$(CH_3)_2$ (known) (A) | 0.1 | 0 |
| $CH_3$—P(=S)(O—⌬)—N=CH—N$(CH_3)_2$ (1) | 0.1 | 100 |
| $CH_3$, ⌬—O, P(=O)—N=CH—N$(CH_3)_2$ (3) | 0.1 | 98 |
| $C_2H_5$, ⌬—O, P(=S)—N=CH—N$(CH_3)_2$ (2) | 0.1 | 98 |

EXAMPLE 4

Critical concentration test/soil insects

Test insect: *Tenebrio molitor* — larvae in the soil had been killed and was 0% if just as many test insects were still alive as in the case of the untreated control.

The active compounds, the amounts used and the results can be seen from Table 4.

Table 4

| Active compound | (*Tenebrio molitor* - larvae in the soil) Degree of destruction in % at an active compound concentration of | |
|---|---|---|
| | 10 ppm | 5 ppm |
| $C_2H_5$, Cl—⌬(Cl)(Cl)—O, P(=S)—N=CH—N$(CH_3)_2$ (known) (C) | 0 | 0 |
| $CH_3$—P(=S)(O—⌬)—N=CH—N$(CH_3)_2$ (1) | 100 | 100 |

Table 4-continued (*Tenebrio molitor* - larvae in the soil)

| Active compound | Degree of destruction in % at an active compound concentration of | |
|---|---|---|
|  | 10 ppm | 5 ppm |
| 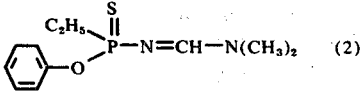 (2) | 100 | 100 |
| 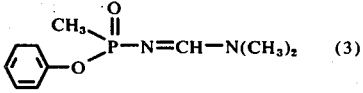 (3) | 100 | 100 |

EXAMPLE 5

The active compounds, the amounts used and the results can be seen from Table 5.

Table 5

(*Phorbia antiqua* - grubs in the soil)

| Active compound | Degree of destruction in % at an active compound concentration of | |
|---|---|---|
|  | 10 ppm | 5 ppm |
| 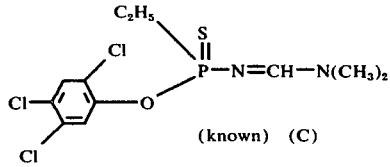 (known) (C) | 50 | 0 |
| 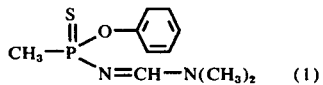 (1) | 100 | 100 |
| 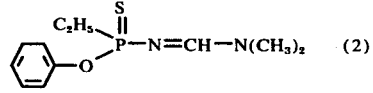 (2) | 100 | 100 |
| 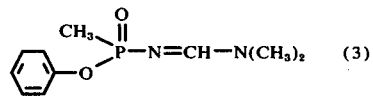 (3) | 100 | 90 |

Critical concentration test/soil insects

Test insect: *Phorbia antiqua* — grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil which is given in ppm (= mg/l), was decisive. The soil was filled into pots and the pots were left to stand at room temperature.

After 24 hours, the test insects were introduced into the treated soil and after a further 2 to 7 days the degree of effectiveness of the active compound was determined in % by counting the dead and live test insects. The degree of effectiveness was 100% if all test insects had been killed and was 0% if just as many test insects were still alive as in the case of the untreated control.

EXAMPLE 6

Critical concentration test

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm (= mg/l), was decisive. The treated soil was filled into pots, lettuce was sown in and the pots were kept at a greenhouse temperature of 27° C.

After 4 weeks, the lettuce roots were examined for infestation with nematodes (root knots), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from Table 6.

Table 6

| Active compound | (Meloidogyne incognita) Degree of destruction in % at an active compound concentration of | |
|---|---|---|
| | 10 ppm | 5 ppm |
| 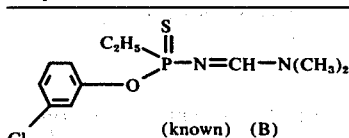 (known) (B) | 0 | 0 |
| 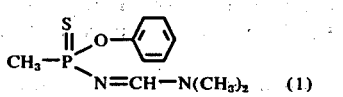 (1) | 100 | 98 |
| 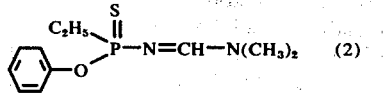 (2) | 100 | 100 |
| 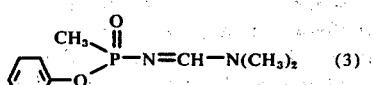 (3) | 100 | 95 |

EXAMPLE 7 a. The O-phenyl(thiono)-alkanephosphonic acid ester amides used as starting materials were prepared as follows:

(IIb)

75 g (0.5 mole) of methane-thionophosphonic acid dichloride were dissolved in 600 cm³ of toluene; a solution of 47 g of phenol and 51 g of triethylamine in 150 cm³ of toluene was added dropwise at −20° to −10° C over the course of 15 minutes. The batch was stirred for 1 hour at 20° C and was then cooled to −10° C. 20 g of ammonia gas were introduced at this temperature. The mixture was stirred for a further hour at 30° C and cooled to 20° C, and the salts were dissolved out by stirring with 500 cm³ of water. The solution was then washed with 500 cm³ of water to which 2 g of sodium hydroxide had been added, and thereafter twice with water, and was dried over sodium sulfate. After evaporating off the solvent in vacuo, an oil remained. The substance was purified by distillation. Boiling point 0.1 mm Hg/130° C; melting point 69° C; yield 52 g (55% of theory).

The following were prepared analogously:

(II)
Melting point: 99° C

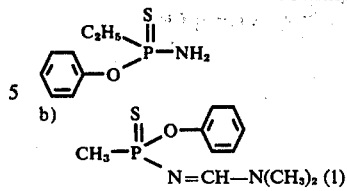
(IIa)
Melting point: 55° C b)

18.7 g (0.1 mole) of O-phenyl-methane-thionophosphonic acid ester amide in 16 g of dimethylformamide-dimethylacetal were stirred for 1 hour at 70° C. The volatile substances were distilled off in vacuo. The residue crystallized on trituration with petroleum ether. 22 g (90.5% of theory) of N,N-dimethyl-N'-[O-phenyl-thiono-methanephosphonyl]-formamidine of melting point 59° C were obtained.

The following compounds were prepared analogously:

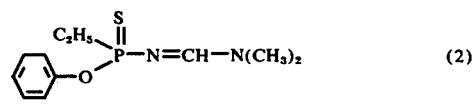
(2)

(78% yield; refractive index $n_D^{20}$. 1.5822

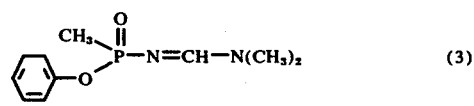
(3)

(90% yield: refractive yield; $n_D^{20}$ : 1.5428)

It will be appreciated that the instant specification and examples are set forth by way of illustration and not limitation, and that various modifications and changes may be made without departing from the spirit and scope of the present invention.

What we claim is:
1. An N,N-dimethyl-N'-[O-phenyl-(thiono)-alkanephosphonyl]-formamidine of the formula

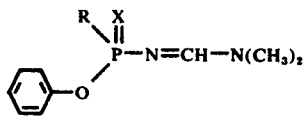

in which
R is alkyl with 1 to 4 carbon atoms, and
X is oxygen or sulfur.

2. The compound according to claim 1 wherein such compound is N,N-dimethyl-N'-[O-phenyl-thionomethanephosphonyl]-formamidine of the formula

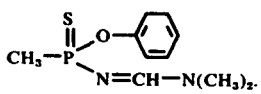

3. The compound according to claim 1 wherein such compound is N,N-dimethyl-N'-[O-phenyl-thionoethanephosphonyl]-formamidine of the formula

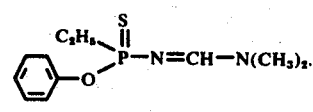

4. The compound according to claim 1 wherein such compound is N,N-dimethyl-N'-[O-phenyl-methanephosphonyl]-formamide of the formula

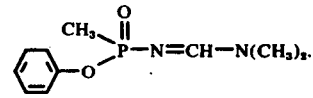

5. An insecticidal, acaricidal or nematocidal composition containing as active ingredient an insecticidally, acaricidally or nematocidally effective amount of a compound according to claim 1 in admixture with a diluent.

6. A method of combating insect, acarid or nematode pests which comprises applying to the pests or a habitat thereof an insecticidally, acaricidally or nematocidally effective amount of a compound according to claim 1.

7. The method according to claim 6 in which said compound is N,N-dimethyl-N'-[O-phenyl-thionomethanephosphonyl]-formamidine, N,N-dimethyl-N'-[O-phenyl-thiono-ethanephosphonyl]-formamidine or N,N-dimethyl-N'-[O-phenyl-methanephosphonyl]-formamidine.

* * * * *